United States Patent [19]

Kimura et al.

[11] Patent Number: 4,849,448

[45] Date of Patent: Jul. 18, 1989

[54] NOVEL BIPHENYL DERIVATIVE AND PREPARATION AND USE THEREOF

[75] Inventors: Masayuki Kimura; Kunio Hosaka; Shigehumi Takeda; Hiroshi Mitsuhashi, all of Tokyo, Japan

[73] Assignee: Tsumura Juntendo, Inc., Japan

[21] Appl. No.: 156,939

[22] PCT Filed: May 27, 1987

[86] PCT No.: PCT/JP87/00339

§ 371 Date: Jan. 19, 1988

§ 102(e) Date: Jan. 19, 1988

[87] PCT Pub. No.: WO87/07272

PCT Pub. Date: Dec. 3, 1987

[30] Foreign Application Priority Data

May 27, 1986 [JP] Japan .................................. 61-120129
Jun. 13, 1986 [JP] Japan .................................. 61-136261
Sep. 30, 1986 [JP] Japan .................................. 61-229767

[51] Int. Cl.$^4$ ...................... A61K 31/36; C07D 317/06
[52] U.S. Cl. ........................................ 514/464; 549/436
[58] Field of Search ........................ 549/436; 514/464

[56] References Cited

FOREIGN PATENT DOCUMENTS 60-209582 10/1985 Japan .

*Primary Examiner*—Nicky Chan

*Attorney, Agent, or Firm*—Burns, Doane, Swecker & Mathis

[57] ABSTRACT

The present invention relates to a novel biphenyl derivative having a liver ailment-moderating action and effective as a remedy for acute hepatitis and chronic hepatitis, a process for the preparation of this biphenyl derivative and a liver ailment-moderating agent comprising this diphenyl derivative as an effective ingredient. This diphenyl derivative is represented by the following formula:

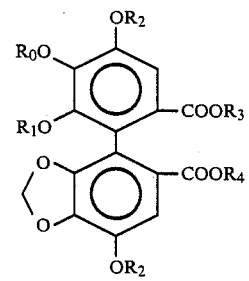

wherein $R_0$ and $R_1$ independently stand for a lower alkyl group or $R_0$ and $R_1$ together represent a group $O=C<$, $R_2$ stands for an alkyl group having 1 to 3 carbon atoms, and $R_3$ and $R_4$ independently stand for a hydrogen atom or a lower alkyl group.

4 Claims, No Drawings

NOVEL BIPHENYL DERIVATIVE AND PREPARATION AND USE THEREOF

TECHNICAL FIELD

The present invention relates to a novel biphenyl derivative having an action of moderating liver ailments, which is effective for remedy of actute hepatitis and chronic hepatitis, a process for the preparation thereof and a liver ailment-moderating agent comprising this derivative as an effective ingredient.

BACKGROUND ART

There are about two million patients suffering from acute hepatitis and chronic hepatitis in Japan, and the development of medicines to remedy these diseases is constantly underway. It is known that a dibenzocyclooctadiene type lignan contained in the fruit of *Schisandra chinesis BAILL* belonging to the genus Schisandraceae is valuable as a remedy for these liver diseases (see Japanese Patent Application No. 60-122560), and the development of a chemical having a higher liver ailment-moderating action is now desired.

DISCLOSURE OF THE INVENTION

The present inventors carried out research with a view to developing a substance having a more effective action of moderating liver ailments and have already found and proposed several compounds (see Japanese Patent Application No. 60-136261). This research was continued, and a novel compound represented by the following formula (I) was found. The present invention was completed on this basis.

More specifically, in accordance with the present invention, there is provided a novel biphenyl derivative represented by the following formula (I):

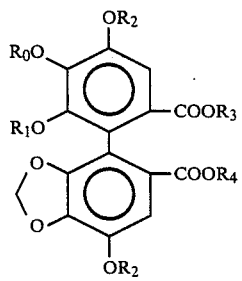
(I)

wherein $R_0$ and $R_1$ independently stand for a lower alkyl group or $R_0$ and $R_1$ together represent a group $O=C<$, $R_2$ stands for an alkyl group having 1 to 3 carbon atoms, and $R_3$ and $R_4$ independently stand for a hydrogen atom or a lower alkyl group.

BEST MODE FOR CARRYING OUT THE INVENTION

Of compounds of the formula (I) where $R_0$ and $R_1$ together form $O=C<$ and $R_3$ is a hydrogen atom, a compound in which $R_4$ is an alkyl group having 1 to 3 carbon atoms is preferred.

Of compounds of the formula (I) where $R_0$ and $R_1$ together for $O=C<$ and $R_3$ is a lower alkyl group, a compound in which $R_2$ is a methyl group and each of $R_3$ and $R_4$ is a methyl group is preferred.

Of compounds of the formula (I) where $R_0$ and $R_1$ stand for a lower alkyl group, a compound in which $R_2$ is a methyl group is preferred, and a compound in which $R_2$ is a methyl group and each of $R_3$ and $R_4$ is an ethyl group is especially preferred.

According to the present invention, the compound of the formula (I) is prepared according to the following procedures.

A compound of the formula (I) in which $R_0$ and $R_1$ together form $O=C<$, $R_3$ is a hydrogen atom and $R_4$ is a lower alkyl group is obtained by reacting a compound represented by the following formula (II):

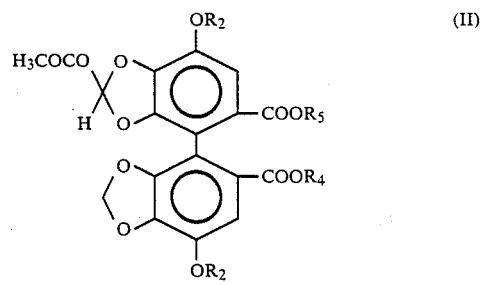
(II)

wherein $R_2$ and $R^4$ are as defined above and $R_5$ stands for an alkyl group, with acetic acid. The compound of the formula (II) is prepared by reacting a compound represented by the following formula (III):

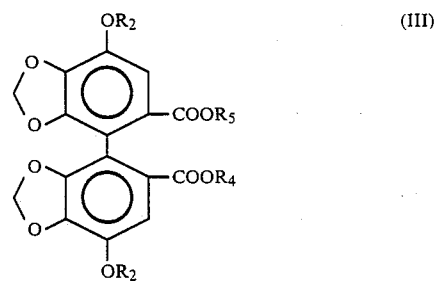
(III)

wherein $R_2$, $R_4$ and $R_5$ are as defined above, with lead tetra-acetate.

A compound of the formula (I) in which $R_0$ and $R_1$ stand for a lower alkyl group or $R_0$ and $R_1$ together form $O=C<$ and $R_3$ is a lower alkyl group is obtained by alkylating a compound represented by the following formula (IV):

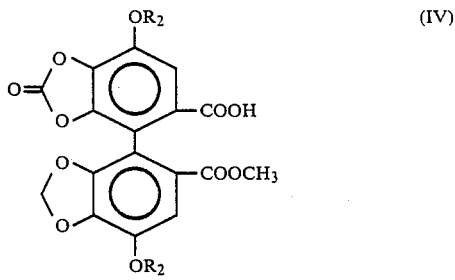
(IV)

wherein $R_2$ is as defined above, that is, a compound of the formula (I) in which $R_0$ and $R_1$ together form $O=C<$, $R_3$ is a hydrogen atom and $R_4$ is a methyl group.

A compound of the formula (I) in which $R_0$ and $R_1$ stand for a lower alkyl group is obtained by alkylating a compound of the following formula (V):

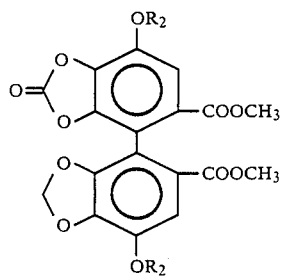

that is, a compound of the formula (I) in which $R_0$ and $R_1$ together form $O=C<$ and $R_3$ and $R_4$ stand for a methyl group.

Furthermore, a compound of the formula (I) in which $R_0$ and $R_1$ stand for a lower alkyl group and $R_3$ and $R_4$ stand for a hydrogen atom is obtained by subjecting a compound of the formula (I) in which $R_0$, $R_1$, $R_3$ and $R_4$ stand for a lower alkyl group, prepared according to the above-mentioned process, to alkali hydrolysis according to customary procedures.

The starting compound of the formula (III) can be obtained according to the process disclosed in the reference [XIE et al, ACTA PHARMACEUTICA SINICA, Vol. 17, No. 1, pages 23–27 (1982)]. More specifically, the compound of the formula (III) is prepared by selectively alkylating one hydroxyl group at the meta-position of a commercially available alkyl ester of gallic acid, reacting the remaining two hydroxyl groups with diiodomethane in the presence of a base to form methylenedioxide, further brominating the 2-position, and carrying out the Ullmann reaction.

Specific examples of the production of the compound of the formula (III) will now be described with reference to the following referential examples.

Referential Example 1

In 2.95 l of a 5% aqueous solution of borax was dissolved 36.8 g of methyl 3,4,5-trihydroxybenzoate, and the solution was stirred at room temperature for 5 hours. Then, 110.5 ml of dimethyl sulfate and a solution of sodium hydroxide were dropped into the solution and the reaction mixture was further stirred for 5 hours. After cooling, the mixture was made acidic by concentrated sulfuric acid and extracted with ethyl acetate. The solvent was removed from the extract to obtain 25.5 g of methyl 5-methoxy-3,4-dihydroxybenzoate (the yield was 64.5%).

Infrared absorption spectrum $\nu_{max}^{KBr}$ cm$^{-1}$ 3444, 1690, 1620, 1600, 1524, 1440, 1338, 1268, 1240, 1108, 1088, 1002, 762

Proton nuclear magnetic resonance spectrum (δ ppm in CDCl$_3$)

3.82 (s, 3H), 3.87 (s, 3H), 7.16 (d, J=2.0, 1H), 7.22 (d, J=2.0, 1H)

Mass spectrum:

m/z (%) 198 (170, M+), 183 (5), 168 (10), 167 (100), 139 (20)

REFERENTIAL EXAMPLE 2

In 600 ml of anhydrous acetone was dissolved 19.8 g of methyl 5-methoxy-3,4-dihydroxybenzoate, and 87 g of anhydrous potassium carbonate and 80.4 g of diiodomethane were added to the solution and the reaction mixture was refluxed for 37 hours. The reaction liquid was filtered and the filtrate was concentrated under a reduced pressure, ethyl acetate was added to the concentrate, the mixture was washed with water, and the solvent was removed to obtain 15.2 g of light yellow crystals. Recrystallization of the crystals from anhydrous ethanol gave 13.6 g of methyl 5-methoxy-3,4-methylenedioxybenzoate (the yield was 65%).

Melting point: 91° C.

Infrared absorption spectrum $\nu_{max}^{KBr}$ cm$^{-1}$ 2956, 2932, 2900, 1706, 1638, 1604, 1506, 1454, 1432, 1368, 1330, 1240, 1188, 1176, 1108, 1038, 988

Proton nuclear magnetic resonance spectrum (δ ppm in CDCl$_3$) 3.88 (s, 3H), 3.93 (s, 3H), 6.04 (s, 2H), 7.20 (d, J=1.5, 1H), 7.33 (d, J=1.5, 1H)

Mass spectrum: m/z (%) 210 (72, M+), 179 (100), 151 (23)

REFERENTIAL EXAMPLE 3

In 35 ml of acetic acid was dissolved 10.5 g of methyl 5-methoxy-3,4-methylenedioxybenzoate, and a solution of bromine (formed by diluting 8 g of bromine with 25 ml of acetic acid) was dropped into the solution over a period of 1 hour. The mixture was stirred at room temperature for 10 hours and the reaction liquid was poured into ice water, and the formed precipitate was recovered by filtration and recrystallized from ethanol to obtain methyl 2-bromo-5-methoxy-3,4-methylenedioxybenzoate (the yield was 51%).

Melting point: 103° to 105° C.

Infrared absorption spectrum $\nu_{max}^{KBr}$ cm$^{-1}$ 2944, 1726, 1626, 1488, 1462, 1434, 1404, 1326, 1248, 1194, 1176, 1108, 1040, 936

Proton nuclear magnetic resonance spectrum (δ ppm in CDCl$_3$) 3.90 (s, 3H), 3.92 (s, 3H), 6.11 (s, 2H), 7.27 (s, 1H)

Mass spectrum: m/z (%) 290 (89, M+), 288 (91, M+), 259 (100), 257 (100)

REFERENTIAL EXAMPLE 4

The crystal consisting of 14.5 g of methyl 2-bromo-5-methoxy-3,4-methylenedioxybenzoate obtained in Referential Example 3 was pulverized and mixed with 70 g of active copper, and the mixture was heated at 80° to 90° C. and dried under a reduced pressure for 3 hours. Then, the pressure was returned to the atmospheric level and the mixture was heated at 146° to 150° C. for 15 hours. The reaction mixture was cooled and extracted with chloroform, the solvent was removed, and the residue was recrystallized from ethanol to obtain 7.5 g of dimethyl 4,4'-dimethoxy-5,6,5',6'-bis(methylenedioxy)-1,1'-biphenyl-6,6'-dicarboxylate (the yield was 72%).

Infrared absorption spectrum $\nu_{max}^{KBr}$ cm$^{-1}$ 1718, 1638, 1594, 1492, 1466, 1436, 1320, 1264, 1242, 1186, 1172, 1136, 1108, 1042, 928

Proton nuclear magnetic resonance spectrum (δ ppm in CDCl$_3$) 3.66 (s, 6H), 3.96 (s, 6H), 5.96 (s, 4H), 7.37 (s, 2H)

Mass spectrum: m/z (%) 418 (100, M+), 359 (22), 328 (13)

In the above-mentioned process of the present invention, first, the compound of the formula (III) was reacted with lead tetra-acetate. As the solvent, there can be mentioned benzene, toluene and xylene, and the reaction was carried out at a temperature ranging from room temperature to the boiling point of the solvent for 3 to 20 hours. Preferably, benzene was used as the solvent and the reaction mixture was refluxed for 5 to 6 hours. After termination of the reaction, the reaction mixture was extracted with a customarily used organic solvent (such as ethyl acetate or petroleum ether) to obtain a compound of the formula (II). Since this reaction occurred in methylene of one methylenedioxy group, the reaction was similarly advanced regardless of the definitions of R$_2$, R$_4$ and R$_5$.

A specific example of the production of the compound of the formula (II) will now be described.

REFERENTIAL EXAMPLE 5

In 50 ml of benzene was dissolved 4.18 g of dimethyl 4,4'-dimethoxy-2,3,2',3'-bis(methylenedioxy)-1,1'-biphenyl-6,6'-dicarboxylate obtained in Referential Example 4, 13.3 g of lead tetra-acetate was added to the solution in a nitrogen current, and the mixture was refluxed for 5 hours. After refluxing, the reaction mixture was cooled to room temperature and extracted with ethyl acetate. The solvent was removed from the extract to obtain 5.12 g of crude dimethyl 2,3-acetoxymethylenedioxy-2',3'-methylenedioxy-4,4'-dimethoxy-1,1'-biphenyl-6,6'-dicarboxylate.

Infrared absorption spectrum $$\nu_{max}^{KBr}$$

cm$^{-1}$ 1760, 1722, 1640

Proton nuclear magnetic resonance spectrum (δ ppm in CDCl$_3$) 2.09 (s, 3H), 3.65 (s, 6H), 3.92 (s, 3H), 3.98 (s, 3H), 5.97 (s, 2H). 7.38 (s, 1H), 7.44 (s, 1H), 7.70 (s, 1H)

Mass spectrum: m/z (%) 476 (13.4), 432 (8.4), 419 (10.4), 418 (44.9), 406 (7.2), 388 (7.4), 375 (20.7), 374 (100), 359 (12.1), 330 (15.2), 315 (13.2), 269 (7.0)

Then, acetic acid was added to the compound of the formula (II) to effect reaction. Preferably, the reaction was carried out under heating and refluxing for 3 to 8 hours. By this reaction, the acetoxy methylenedioxy group was converted to a cyclic carbonate, and simultaneously, the alkyl ester on the side of the cyclic carbonate was hydrolyzed to a carboxylic acid. As a result, the compound of the formula (I) was precipitated in the reaction liquid, and accordingly, the compound of the formula (I) could be easily isolated by the customary filtration operation. For the same reason as described above, this reaction was similarly advanced regardless of the definitions of R$_2$, R$_4$ and R$_5$.

The production of the compound of the formula (I) will now be described with reference to the following examples.

EXAMPLE 1

In 50 ml of 80% acetic acid was dissolved 5.12 g of crude dimethyl 2,3-acetoxymethylenedioxy-2',3'-methylenedioxy-4,4'-dimethoxy-1,1'-biphenyl-6,6'-dicarboxylate obtained in Referential Example 5, and the solution was refluxed for 5 hours. After refluxing, the reaction mixture was cooled and subjected to suction filtration to obtain 3.1 g of 2,3-oxomethylenedioxy-2',3'-methylenedioxy-4,4'-dimethoxy-6'-methyoxycarbonyl-1,1'-biphenyl-6-carboxylic acid (the overall yield was 74.3%).

Infrared absorption spectrum $$\nu_{max}^{KBr}$$

cm$^{-1}$ 3392, 1716, 1624, 1574, 1500, 1488, 1462, 1434, 1412, 1400, 1338, 1284, 1262, 1220, 1172, 1092, 1040, 1018, 776

Proton nuclear magnetic resonance spectrum (δ ppm in CDCl$_3$) 3.83 (s, 3H), 4.00 (s, 3H), 4.01 (s, 3H), 6.14 (s, 2H), 7.22 (s, 1H), 7.65 (s, 1H)

Mass spectrum: m/z (%) 374 (100, M-44), 343 (9.4), 335 (6.0), 329 (11.5), 328 (12.9), 315 (20.1), 313 (8.5), 287 (12.5), 285 (7.9), 275 (8.2), 272 (9.4), 271 (10.1), 269 (19.9), 257 (8.2)

The starting compounds of the formulae (IV) and (V) were, of course, prepared through the compounds of the formulae (III) and (II) in the same manner as described above.

Alkylation of the compound (IV) could be accomplished by using an alkylating agent such as dimethyl sulfate or methyl iodide.

Where dimethyl sulfate was used, the reaction was carried out in a solvent such as methanol, ethanol or propanol at a temperature in the range of from room temperature to the boiling point of the used solvent for 1 to 12 hours. In order to increase the reactivity, preferably a base such as potassium carbonate or sodium carbonate was added. A dissolution assistant such as DMSO (dimethylsulfoxide) could be added to the solvent.

Where methyl iodide was used, the reaction was carried out in a solvent such as acetone, methanol, ethanol or propanol at room temperature to about 40° C. for about 5 to 25 hours. In order to increase the reactivity, preferably a base such as potassium carbonate or sodium carbonate was added.

The above-mentioned two alkylation processes may be combined according to need.

After termination of the reaction, the intended product could be easily obtained by extraction with ethyl acetate, ether or the like. Moreover, recrystallization from benzene, hexane or the like could be adopted.

The alkylation of the compounds of the formulae (IV) and (V) also could be accomplished by reacting them with an alkylating agent in an alcohol as the solvent. As the alcohol, there can be mentioned methanol, ethanol, propanol, isopropanol, n-butanol, isobutanol, sec-butanol, tert-butanol, n-pentanol, isopentanol and n-hexanol. As the alkylating agent, there can be mentioned dimethyl sulfate, diethyl sulfate and alkyl halides having 1 to 7 carbon atoms. If necessary, a base such as potassium carbonate, sodium carbonate or sodium hydroxide could be added to promote the reaction, or a dissolution assistant such as DMSO could be added.

The reaction temperature was in the range of from room temperature to the boiling point of the used alcohol. The reaction was completed within about 3 to 100 hours. After termination of the reaction, the intended product could be easily obtained by extraction with ethyl acetate, either or the like, and recrystallization from an ordinary solvent such as benzene or hexane could be adopted. Moreover, purification could be performed by a customary column chromatography.

The preparation of the compound of the formula (I) by the alkylation of the compound of the formula (IV) or (V) will now be described with reference to the following examples.

EXAMPLE 2

In methanol and DMSO was dissolved 2.59 g of 2,3-oxomethylenedioxy-2',3'-methylenedioxy-4,4'-dimethoxy-6'-methoxycarbonyl-1,1'-biphenyl-6-carboxylic acid obtained in Example 1, and 8.6 of potassium carbonate and 7.8 g of dimethyl sulfate were added to the solution and the mixture was refluxed for 8 hours. The reaction mixture was cooled and methanol was removed, the residue was extracted with ethyl acetate, and the ethyl acetate was removed from the extract. Recrystallization of the residue from benzene gave dimethyl 2',3'-methylenedioxy-2,3,4,4'-tetramethoxy-1,1'-biphenyl-6,6'-dicarboxylate having the following physical properties (the yield was 79.5%).

Infrared absorption spectrum $$\nu_{max}^{KBr}$$

$cm^{-1}$ 1722, 1638, 1594, 1492, 1462, 1434, 1394, 1338, 1324, 1274, 1244, 1218, 1188, 1168, 1126, 1100, 1042, 992

Proton nuclear magnetic resonance spectrum (δ ppm in CDCl$_3$) 3.61 (s, 6H), 3.65 (s, 3H), 3.93 (s, 3H), 3.94 (s, 3H), 3.97 (s, 3H), 5.96 (d, J=2.44, 2H), 7.37 (s, 1H), 7.39 (s, 1H)

Mass spectrum: m/z (%) 434 (100), 403 (12.2), 375 (9.0), 373 (6.6), 360 (7.4), 359 (5.3), 345 (9.1), 344 (10.5), 343 (9.0), 329 (7.2), 315 (6.7), 223 (44.9)

EXAMPLE 3

In 10 ml of acetone was dissolved 100 mg of 2,3-oxomethylenedioxy-2',3'-methylenedioxy-4,4'-dimethoxy-6'-methoxycarbonyl-1,1'-biphenyl-6-carboxylic acid obtained in Example 1, 60 mg of potassium carbonate and 68 mg of methyl iodide were added to the solution, and the mixture was stirred at room temperature for 12 hours. After termination of the reaction, acetone was removed from the reaction mixture, and the residue was extracted with ethyl acetate. The solvent was removed from the extract to obtain dimethyl 2,3-oxomethylenedioxy-2',3'-methylenedioxy-4,4'-dimethoxy-1,1'-biphenyl-6,6'-dicarboxylate having the following physical properties (the yield was 94.5%).

Infrared absorption spectrum $$\nu_{max}^{KBr}$$

$cm^{-1}$ 1726, 1634, 1600, 1568, 1484, 1432, 1408, 1392, 1368, 1342, 1278, 1246, 1226, 1194, 1172, 1140, 1108, 1034, 974, 928, 774

Proton nuclear magnetic resonance spectrum (δ ppm in CDCl$_3$) 3.84 (s, 3H), 3.96 (s, 3H), 4.01 (s, 3H), 4.03 (s, 3H), 6.14 (s, 2H), 7.21 (s, 1H), 7.64 (s, 1H)

Mass spectrum: m/z (%) 389 (21.6, M+-43), 388 (100, M+-44), 373 (8.4), 357 (6.2), 343 (7.4), 342 (8.4), 329 (7.1), 314 (8.0), 302 (6.5), 271 (5.8)

EXAMPLE 4

In methanol was dissolved 50 mg of dimethyl 2,3-oxomethylenedioxy-2',3'-methylenedioxy-4,4'-dimethoxy-1,1'-biphenyl-6,6'-dicarboxylate obtained in Example 3, potassium carbonate and dimethyl sulfate were added to the solution, and the mixture was refluxed for 2 hours. After the reaction, the reaction mixture was extracted with ethyl acetate and the ethyl acetate was removed from the extract to obtain dimethyl 2',3'-methylenedioxy-2,3,4,4'-tetramethoxy-1,1'-biphenyl-6,6'-dicarboxylate (the yield was 100%). The physical properties were in agreement with those of the compound obtained in Example 2.

EXAMPLE 5

In 5 ml of DMSO were suspended 209 mg of 2,3-oxomethylenedioxy-2',3'-methylenedioxy-4,4'-dimethoxy-6'-methoxycarbonyl-1,1'-biphenyl-6-carboxylic acid obtained in Example 1 and 15 ml of methanol, and 346 mg of potassium carbonate and 386 mg of diethyl sulfate were added to the suspension. The mixture was refluxed for 5 hours, and the solvent was removed and the residue was extracted with ethyl acetate. The extract was dried and the obtained oily product was recrystallized to obtain 195 mg of dimethyl 2,3-diethoxy-4,4'-dimethoxy-2',3'-methylenedioxy-1,1'-biphenyl-6,6'-dicarboxylate having the following physical properties (the yield was 84%).

Melting point: 107° to 108° C.

Infrared absorption spectrum $$\nu_{max}^{KBr}$$

$cm^{-1}$ 1722, 1642, 1598, 1486, 1464, 1434, 1414, 1384, 1350, 1322, 1268, 1244, 1192, 1044

Proton nuclear magnetic resonance spectrum (δ ppm in CDCl$_3$) 1.00 (t, J=7.08 Hz, 3H), 1.37 (t, J=7.08 Hz, 3H), 3.60 (s, 3H), 3.66 (s, 3H), 3.81 (q, d, J=7.08, 4.88 Hz, 2H), 3.92 (s, 3H), 3.97 (s, 3H), 4.15 (q, J=7.08 Hz, 2H), 5.97, 5.93 (AB, J=1.47 Hz, 2H), 7.36 (s, 1H), 7.37 (s, 1H)

Mass spectrum: m/z (%) 462 (62, M+), 434 (18), 418 (23), 402 (23), 374 (100), 359 (15), 345 (18), 343 (22), 331 (12), 329 (17), 328 (15), 315 (23), 302 (16), 287 (11), 271 (13), 237 (67), 205 (14)

EXAMPLE 6

In 25 ml of DMSO were suspended 1.25 g of 2,3-oxomethylenedioxy-2',3'-methylenedioxy-4,4'-dimethoxy-6'-methoxycarbonyl-1,1'-biphenyl-6-carboxylic acid obtained in Example 1 and 75 ml of ethanol, and 2.1 g of potassium carbonate and 2.3 g of ethyl sulfate were added to the suspension. The mixture was refluxed for 2 days and the solvent was removed, the residue was extracted with ethyl acetate, and the extract was dried. The obtained oily product was subjected to flash column chromatography (silica: Merk 60, solvent: ethyl acetate/n-hexane (1:1), pressure: 0.5 kg/cm$^2$) to effect purification and obtain 970 mg of diethyl 2,3-diethoxy-4,4'-dimethoxy-2',3'-methylenedioxy-1,1'-biphenyl-6,6'-dicarboxylate having the following physical properties (the yield was 66%).

Melting point: 73.0° to 74.5° C.

Infrared absorption spectrum $$\nu_{max}^{KBr}$$

$cm^{-1}$ 1712, 1642, 1596, 1484, 1464, 1442, 1414, 1386, 1370, 1346, 1334, 1318, 1298, 1242, 1178, 1102, 1042

Proton nuclear magnetic resonance spectrum (δ ppm in CDCl$_3$) 0.98 (t, J=7.08 Hz, 3H), 1.02 (t, J=7.08 Hz, 3H), 1.03 (t, J=7.08 Hz, 3H), 1.38 (t, J=7.08 Hz, 3H), 3.83 (q, J=7.08 Hz, 2H), 3.91 (s, 3H), 3.97 (s, 3H), 4.03 (q, d, J=7.08, 3.42 Hz, 2H), 4.08 (q, J=7.08 Hz, 2H), 4.13 (q, J=7.08 Hz, 2H), 5.95, 5.98 (AB, J=1.22 Hz, 2H), 7.37 (s, 1H), 7.37 (s, 1H)

Mass spectrum: m/z (%) 490 (100, M+), 476 (11), 416 (14), 388 (28), 371 (10), 359 (11), 343 (13), 315 (13), 252 (11), 251 (74), 223 (30)

EXAMPLE 7

In 30 ml of DMSO were dissolved 1.3 g of dimethyl 2,3-oxomethylenedioxy-2',3'-methylenedioxy-4,4'-dimethoxy-1,1'-biphenyl-6,6'-dicarboxylate and 70 ml of methanol, and 2 g of potassium carbonate and 2.2 g of diethyl sulfate were added to the solution and the mixture was refluxed overnight. After termination of the reaction, the reaction mixture was extracted with ethyl acetate and the extract was dried to obtain an oily product. The oily product was recrystallized from ethyl acetate to obtain 966 mg of dimethyl 2-ethoxy-2',3'-methylenedioxy-3,4,4'-trimethoxy-1,1'-biphenyl-6,6'-dicarboxylate having the following physical properties (the yield was 74.5%).

Melting point: 93° to 94° C. Infrared absorption spectrum $\nu_{max}^{KBr}$, cm$^{-1}$ 1720, 1642, 1598, 1486, 1464, 1432, 1414, 1384, 1350, 1322, 1270, 1246, 1192, 1174, 1124, 1102, 1046

Proton nuclear magnetic resonance spectrum (δ ppm in CDCl$_3$)

1.01 (t, J=7.08 Hz, 3H), 3.61 (s, 3H), 3.66 (s, 3H), 3.80 (q, d, J=7.08, 2.69 Hz, 2H), 3.93 (s, 6H), 3.98 (s, 3H), 5.95, 5.97 (AB, J=1.46 Hz, 2H), 7.36 (s, 1H), 7.38 (s, 1H)

Mass spectrum: m/z (%) 448 (100, M+), 434 (10), 418 (12), 389 (18), 388 (45), 373 (13), 357 (12), 329 (10), 237 (65), 205 (14)

EXAMPLE 8

In 35 ml of DMSO were dissolved 1.72 g of dimethyl 2,3-oxomethylenedioxy-2',3'-methylenedioxy-4,4'-dimethoxy-1,1'-biphenyl-6,6'-dicarboxylate and 100 ml of ethanol, and 2.76 g of potassium carbonate and 2.52 g of dimethyl sulfate were added to the solution and the mixture was refluxed overnight. After termination of the reaction, the reaction mixture was extracted and the extract was dried. The obtained oily product was purified by flash column chromatography (silica gel: Merk 60, solvent: ethyl acetate/n-hexane (3:2), pressure: 0.5 kg/cm$^2$) to obtain 1.16 g of diethyl 2',3'-methylenedioxy-2,3,4,4'-tetramethoxy-1,1'-biphenyl-6,6'-dicarboxylate having the following physical properties (the yield was 73%).

Melting point: 95.0° to 96.5° C.
Infrared absorption spectrum $\nu_{max}^{KBr}$, cm$^{-1}$ 1712, 1642, 1596, 1486, 1462, 1428, 1398, 1370, 1334, 1320, 1300, 1244, 1192, 1178, 1126, 1102, 1044

Proton nuclear magnetic resonance spectrum (δ ppm in CDCl$_3$) 0.99 (t, J=7.08 Hz, 3H), 1.05 (t, J=7.08 Hz, 3H), 3.63 (s, 3H), 3.94 (s, 6H), 3.98 (s, 3H), 4.04 (q, J=7.08 Hz, 2H), 4.07 (q, J=7.05 Hz, 2H), 5.96, 5.99 (AB, J=1.46 Hz, 2H), 7.38 (s, 1H), 7.39 (s, 1H)

Mass spectrum: m/z (%) 462 (100, M+), 345 (14), 344 (11), 329 (10), 237 (16), 209 (30)

EXAMPLE 9

In 60 ml of n-propanol and 20 ml of DMSO was dissolved 980 mg of dimethyl 2,3-oxomethylenedioxy-2',3'-methylenedioxy-4,4'-dimethoxy-1,1'-biphenyl-6,6'-dicarboxylate, and 1.57 g of potassium carbonate and 1.75 g of diethyl sulfate were added to the solution and the mixture was refluxed for 5 hours. After completion of the reaction, the reaction mixture was extracted with ethyl acetate and the extract was dried to obtain an oily product. The oily product was purified by flash column chromatography (silica gel: Merk 60, solvent: ethyl acetate/n-hexane (1:1), pressure: 0.5 kg/cm$^2$) to obtain 645 mg of methyl 2-ethoxy-2',3'-methylenedioxy-6-propoxycarbonyl-3,4,4'-trimethoxy-1,1'-biphenyl-6'-carboxylate having the following physical properties (the yield was 60%).

Melting point: 74.5° to 76° C.
Infrared absorption spectrum $\nu_{max}^{KBr}$, cm$^{-1}$ 1720, 1642, 1598, 1486, 1464, 1428, 1414, 1386, 1350, 1336, 1320, 1268, 1244, 1192, 1176, 1102, 1042

Proton nuclear magnetic resonance spectrum (δ ppm in CDCl$_3$) 0.75 (t, J=7.33 Hz, 3H), 1.01 (t, J=7.08 Hz, 3H), 1.40 (m, 2H), 3.65 (s, 3H), 3.80 (q, d, J=7.08, 1.95 Hz, 2H), 3.92 (s, 6H), 3.97 (s, 3H), 3.92–3.97 (2H, 5.95, 5.97 (AB, J=1.22 Hz, 2H), 7.37 (s, 1H), 7.38 (s, 1H)

Mass spectrum: m/z (%) 476 (100, M+), 462 (12), 389 (19), 388 (43), 373 (12), 575 (15), 329 (17), 265 (17), 224 (11), 223 (90)

EXAMPLE 10

In 45 ml of n-propanol and 15 ml of DMSO was dissolved 748 mg of dimethyl 2,3-oxomethylenedioxy-2',3'-methylenedioxy-4,4'-dimethoxy-1,1'-biphenyl-6,6'-dicarboxylate obtained in Example 3, and 1.19 g of potassium carbonate and 1.33 g of diethyl sulfate were added to the solution and the mixture was refluxed for 2 days. After termination of the reaction, the reaction mixture was extracted with ethyl acetate and the extract was dried, and the obtained oily product was purified by flash column chromatography (silica gel: Merk 60, solvent: ethyl acetate/n-hexane (1:1), pressure 0.5 kg/cm$^2$) to obtain 495 mg of dipropyl 2-ethoxy-2',3'-methylenedioxy-3,4,4'-trimethoxy-1,1'-biphenyl-6,6'-carboxylate having the following physical properties (the yield was 57%).

Melting point: 41° to 42° C.
Infrared absorption spectrum $\nu_{max}^{KBr}$, cm$^{-1}$ 1714, 1642, 1596, 1486, 1464, 1428, 1414, 1390, 1350, 1320, 1242, 1178, 1102, 1042

Proton nuclear magnetic resonance spectrum (δ ppm in CDCl$_3$) 0.74 (t, J=7.33 Hz, 3H), 0.79 (t, J=7.33 Hz, 3H), 1.01 (t, J=7.08 Hz, 3H), 1.33–1.49 (m, 4H), 3.80 (q, d, J=7.08, 1.71 Hz, 2H), 3.96 (t, J=6.38 Hz, 2H9, 3.99 (t, J=6.83 Hz, 2H), 3.92 (s, 3H), 3.93 (s, 3H), 3.97 (s, 3H), 5.94, 5.97 (AB, J=1.46 Hz, 2H), 7.38 (s, 1H), 7.39 (s, 1H)

Mass spectrum: m/z (%) 504 (89, M+), 490 (14), 417 (13), 416 (32), 359 (11), 357 (15), 331 (12), 330 (11), 329 (18), 315 (11), 365 (22), 224 (12), 223 (100)

A compound of the formula (I) in which $R_1$ is a lower alkyl group and $R_3$ and $R_4$ stand for a hydrogen atom could be obtained by alkali hydrolysis of a compound of the formula (I) in which $R_1$, $R_3$ and $R_4$ stand for a lower alkyl group. The alkali hydrolysis could be performed according to ordinary procedures customarily adopted. As the base used for the alkali hydrolysis, there can be mentioned potassium hydroxide and sodium hydroxide.

The preparation of the biphenyl derivative by the alkali hydrolysis will now be described in detail with reference to the following examples.

EXAMPLE 11

In 50 ml of dioxane was dissolved 1.3 g of dimethyl 2′,3′-methylenedioxy-2,3,4,4′-tetramethoxy-1,1′-biphenyl-6,6′-dicarboxylate obtained in Example 2, and 10 mg of 5% potassium hydroxide was added to the solution. The mixture was heated at 70° C. and stirred overnight. When the pH value of the mixture was adjusted to 1 by 3N hydrochloric acid, crystals were precipitated. The precipitated crystals were recovered by filtration and recrystallized from ethanol to obtain 1.12 g of 2′,3′-methylenedioxy-2,3,4,4′-tetramethoxy-1,1′-biphenyl-6,6′-dicarboxylic acid having the following physical properties (the yield was 92%).

Melting point: 257.7° to 259° C.

Infrared absorption spectrum $$\nu_{max}^{KBr}$$

cm$^{-1}$ 3000–2500, 1690, 1638, 1594, 1492, 1454, 1422, 1392, 1324, 1270, 1234, 1196, 1156, 1130, 1104, 1038, 984, 928

Proton nuclear magnetic resonance spectrum ($\delta$ ppm in CDCl$_3$) 3.16 (s, 3H), 3.94 (s, 3H), 3.95 (s, 3H), 3.98 (s, 3H), 5.99, 6.00 (AB, J=1.47 Hz, 2H), 7.43 (s, 1H, 7.46 (s, 1H)

FD mass spectrum: m/z (%) 434 (M+)

EXAMPLE 12

In 4 ml of dioxane was dissolved 49 mg of diethyl 2,3-diethoxy-4,4′-dimethoxy-2′,3′-methylenedioxy-1,1′-biphenyl-6,6′-dicarboxylate obtained in Example 6, and 1 ml of a 5% aqueous solution of potassium hydroxide was added to the solution. The mixture was heated at 70° C. and stirred overnight. The pH value was adjusted to 1 to 2 by 3N hydrochloric acid, the reaction mixture was extracted with chloroform, and the solvent was removed from the extract to obtain 38 mg of 2,3-diethoxy-4,4′-dimethoxy-2′,3′-methylenedioxy-1,1′-biphenyl-6,6′-dicarboxylic acid having the following physical properties (the yield was 88%).

Melting point: 262° to 263° C.

Infrared absorption spectrum $$\nu_{max}^{KBr}$$

cm$^{-1}$ 2750–2500, 1696, 1640, 1598, 1486, 1464, 1438, 1414, 1384, 1328, 1278, 1252, 1196, 1160, 1128, 1102, 1038

Proton nuclear magnetic resonance spectrum ($\delta$ ppm in CDCl$_3$) 0.98 (t, J=7.08 Hz, 3H), 1.32 (t, J=7.08 Hz, 3H), 3.6–3.9 (m, 2H), 3.92 (s, 3H), 3.97 (s, 3H), 4.15 (q, J=7.08 Hz, 2H), 5.94, 5.98 (AB, J=1.22 Hz, 2H), 7.42 (s, 1H), 7.45 (s, 1H)

FD mass spectrum: m/z (%) 434 (M+)

EXAMPLE 13

In 4 ml of dioxane was dissolved in 48 mg of methyl 2-ethoxy-2′,3′-methylenedioxy-6-propoxycarbonyl-3,4,4′-trimethoxy-1,1′-biphenyl-6′-carboxylate obtained in Example 9, and 1 ml of a 5% aqueous solution of potassium hydroxide was added to the solution. The mixture was heated at 70° C. and stirred overnight, the pH value was adjusted to 1 by 3N hydrochloric acid, and the mixture was extracted with chloroform. The solvent was removed from the extract to obtain 36 mg of 2-ethoxy-2′,3′-methylenedioxy-3,4,4′-trimethoxy-1,1′-biphenyl-6,6′-dicarboxylic acid having the following physical properties (the yield was 86%).

Melting point: 236° to 237° C.

Infrared absorption spectrum $$\nu_{max}^{KBr}$$

cm$^{-1}$ 2700–2400, 1694, 1642, 1600, 1486, 1462, 1414, 1384, 1322, 1284, 1260, 1196, 1180, 1158, 1130, 1102

Proton nuclear magnetic resonance spectrum ($\delta$ ppm in CDCl$_3$) 0.97 (t, J=7.08 Hz, 3H), 3.7–4.0 (m, 2H), 3.91 (s, 6H), 3.96 (s, 3H), 5.94, 5.98 (AB, J−1.22 Hz, 2H), 7.41 (s, 1H), 7.44 (s, 1H)

FD mass spectrum: m/z (%) 420 (M+)

INDUSTRIAL APPLICABILITY

The following effects can be obtained according to the present invention.

(1) The compound of the formula (I) according to the present invention has an action of moderating liver ailments and is effective for curing liver diseases.

(2) The intended compound can be obtained in a high yield according to the process of the present invention and can be purified by recrystallization, and since the operation is simple, the process of the present invention is suitable for industrial purposes.

(3) According to the process of the present invention, only one methylenedioxy group can be selectively cleft in a high yield.

(4) Selective ester exchange is possible according to the process of the present invention.

(5) An optional alkyl group can be introduced into the alkylether group at the 2-position of the formula (I) by selecting an appropriate alkylating agent.

The liver ailment-improving action of the compound of the formula (I) will now be described with reference to the following experiments.

Experiment 1

Male SD strain rats of 7 weeks old were used as 10 animals in each group after the fasting for 24 hours. Each of the compounds oftained in Examples 1 through 3 and 5 through 10 was suspended in 1% Tween 80/physiological saline solution and administered at 30 or 100 mg/kg intraperitoneally. After 30 minutes, 4 mg/kg of a 25% carbon tetrachloride/olive oil mixture was orally administered to the rats. After 24 hours, blood was collected and the liver was extracted. In the control group, the above procedure were repeated in the same manner except that the compounds obtained in Examples 1 through 3 and 5 through 10 were not added.

As the result, it was found that, although the sGPT value (serum Glutamic Pyruvic Transaminase) in the control group was 6690±979, the sGPT values of the group to which 30 mg/kg of the compound obtained in Example 1 was administered, the group to which 100 mg/kg of the compound obtained in Example 1 was administered, the group to which 30 mg/kg of the compound obtained in Example 2 was administered, the group to which 100 mg/kg of the compound obtained in Example 2 was administered, the group to whih 30 mg/kg of the compound obtained in Example 3 was administered and the group to which 100 mg/kg of the compound obtained in Example 3 was administered, were 3372±772, 2620±340, 2030±295, 1675±357, 2845±340 and 1220±540, respectively.

The results obtained in the groups to which the compounds obtained in Examples 5 through 10 were administered at 100 mg/kg are shown in Table 1.

TABLE 1

| Test Compounds | sGPT Values (units/l) |
| --- | --- |
| Normal | 17.4 ± 0.9 |
| Control | 1082.2 ± 185.6 |
| compound obtained in Example 5 | 372.0 ± 35.6 |
| compound obtained in Example 6 | 154.7 ± 32.3 |
| compound obtained in Example 7 | 345.7 ± 47.4 |
| compound obtained in Example 8 | 260.2 ± 42.2 |
| compound obtained in Example 9 | 477.0 ± 58.8 |
| compound obtained in Example 10 | 303.1 ± 73.8 |

From these results, it was confirmed that the compounds of the formula (I) according to the present invention has an improving action against liver injury.

Experiment 2

Male SD strain rats of 7 weeks old were used as animals in each group after the fasting for 24 hours. Each of the compounds in Examples 2, 6 and 8 was suspended in 1% Tween 80/water solution and administered at 100 mg/kg orally. After 30 minutes, 2 ml/kg of a 25% carbon tetrachloride/olive oil mixture was intraperitoneally administered. After 24 hours, blood was collected from the celiac artery, and the sGOP values (serum Glutamic Oxaloacetic Transaminase) and sGPT were determined. The results are shown in Table 2.

TABLE 2

| Test Compounds | sGOP Values (units/l) | sGPT Values (units/l) |
| --- | --- | --- |
| Normal | 67.2 ± 3.3 | 11.4 ± 0.8 |
| Control | 7704.4 ± 1281.3 | 981.4 ± 158.5 |
| compound obtained in Example 2 | 6204.0 ± 1133.2 | 424.4 ± 80.4 |
| compound obtained in Example 6 | 5189.0 ± 698.9 | 191.9 ± 38.0 |
| compound obtained in Example 8 | 5602.0 ± 1580.1 | 447.3 ± 164.0 |

When the compounds obtained in Examples 5 through 13 were orally administered to male ddy strain mice as 10 animals in each group, it was found that none of the mice died up to 1000 mg/kg.

In view of these results, it is deemed preferable to administer the drug for liver injuries of the present invention at a daily dose of 5 to 80 mg in the case of the oral administration or 0.1 to 10 mg in the case of non-oral administration, as the weight of the compounds of the formula (I), for adults this should be divided into several dosages.

The compound of the formula (I) can be formed into various preparations such as liquids, powders, granules, tablets, enteric coatings and capsules by using appropriate solvents, excipients and adjuvants according to customary procedures.

The compound of formula (I) may be mixed with other pharmaceutically active components in forming a preparation.

For the purpose of oral administration, the compound of the formula (I) can be formed into tablets, pills, capsules, powders, granules and the like by using at least one excipient selected from starch, lactose, refined sugar, mannitol, carboxymethyl cellulose and the like.

For the above-mentioned preparations, in addition to the excipient, there may be used brighteners such as magnesium stearate, sodium lauryl sulfate and talc, binders such as dextrin, crystalline cellulose, polyvinyl pyrrolidone, gum arabic, corn starch and gelatin, disintegrating agents such as sodium cellulose glucolate, potassium cellulose glucolate, potato starch and carboxymethyl cellulose, and flowability improvers such as soft anhydrous silicic acid. Moreover, the medicine of the present invention can be administered in the form of a suspension, an emulsion, a syrup or an elixir, for which a taste improver, a smell improver or a colorant may be used.

In preparing an injection, distilled water for injection, a physiological saline soltion, an aqueous solution of dextrose, a vegetable oil for injection, propylene glycol and polyethylene glycol can be ordinarily used as the diluent. An isotonic agent, a stabilizer, an antiseptic agent, an analgesic agent and the like may be added according to need. Preferably, the preparation of this type is dissolved in a sterilized injection solution.

The liver ailment-moderating agent of the present invention will now be described in detail with reference to the following examples.

EXAMPLE 14

The compound obtained in Example 5 was finely divided, and 0.5 g of the fine powder was mixed with 98.5 g of lactose and 1 g of magnesium stearate. The mixture was formed into slug tablets having a diameter of 20 mm and a weight of 2.3 g by a one-shot slug tableting machine. The tablets were pulverized by an oscillator, and the particle size was adjusted and the pulverization product was sieved to obtain good granules having a particle size of 20 to 50 mesh.

The granules contained 5 mg of the compound obtained in Example 5 per gram of the granules. The granules were administered at a dose of 1 to 5 g three times a day according to the condition of the patient.

EXAMPLE 15

The compound obtained in Example 6 was finely divided, and 0.5 g of the finely divided compound was mixed with 98.5 g of lactose and 1 g of magnesium stearate, and the mixture was formed into slug tablets having a diameter of 20 mm and a weight of 2.3 g by a one-shot slug tableting machine. The tablets were pulverized by an oscillator, and the particle size was adjusted and the pulverization product was sieved to obtain good granules having a size of 20 to 50 mesh.

The granules contained 5 mg of the compound obtained in Example 6 per gram of the granules. The granules were administered at a dose of 1 to 5 g three times a day according to the condition of the patient.

EXAMPLE 16

To 2.5 g of the compound obtained in Example 7 were added 93 g of microcrystalline cellulose, 3 g of sodium cellulose glucolate and 1.5 g of magnesium stearate, and the mixture was formed into tablets having a diameter of 9 mm and a weight of 200 mg by a one-shot tableting machine.

Each tablet contained 5 mg of the compound obtained in Example 7. One to five tablets were administered three times a day according to the condition of the patient.

EXAMPLE 17

To 2.5 g of the compound obtained in Example 8 were added 93 g of microcrystalline cellulose, 3 g of sodium cellulose glycolate and 1.5 g of magnesium stearate, and the mixture was formed into tablets having a diameter of 9 mm and a weight of 200 mg by a one-shot tableting machine.

Each tablet contained 5 mg of the compound obtained in Example 8, and one to five tablets were administered three times a day according to the condition of the patient.

EXAMPLE 18

The compound obtained in Example 9 was finely divided, and 5 g of the finely divided compound was mixed with 91.5 g of lactose, 0.5 g of soft anhydrous silicic acid and 3 g of microcrystalline cellulose. The mixture was filled in hard capsules in an amount of 100 mg per capsule.

Each capsule contained 5 mg of the compound obtained in Example 9. One to two capsules were administered three times a day according to the condition of the patient.

EXAMPLE 19

The compound obtained in Example 10 was finely divided, and 5 g of the finely divided compound was mixed with 91.5 g of lactose, 0.5 g of soft anhydrous silicic acid and 3 g of microcrystalline cellulose. The mixture was filled in hard capsules in an amount of 100 mg per capsule.

Each capsule contained 5 mg of the compound obtained in Example 10, and one to two capsules were administered three times a day according to the condition of the patient.

EXAMPLE 20

In a sterilized vial, 10 mg of the compound obtained in Example 12 was filled and sealed. At the time of application, the compound was dissolved in a 5% solution of glucose or a physiological saline solution, and 500 ml of the formed transfusion liquid was intravenously drip-administered over a period of 2 to 4 hours.

EXAMPLE 21

In a sterilized vial, 10 mg of the compound obtained in Example 13 was filled and sealed. At the time of application, the compound was dissolved in a 5% solution of glucose or a physiological saline solution, and 500 ml of the formed transfusion liquid was intravenously drip-administered over a period of 2 to 4 hours.

We claim:

1. A biphenyl derivative represented by the following formula (I):

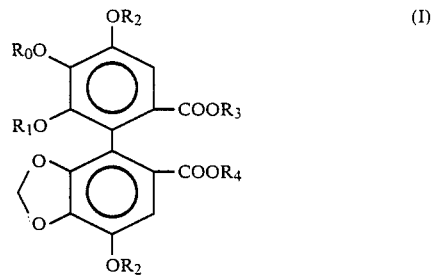

wherein $R_0$ and $R_1$ independently stand for a lower alkyl group, $R_2$ stands for an alkyl group having 1 to 3 carbon atoms, and $R_3$ and $R_4$ independently stand for a hydrogen atom or a lower alkyl group.

2. The compound as set forth in claim 1, wherein $R_2$ is a methyl group.

3. A compound as set forth in claim 2, wherein $R_3$ and $R_4$ stand for an ethyl group.

4. A liver ailment-moderating composition comprising an effective amount of a biphenyl derivative represented by the following formula (I):

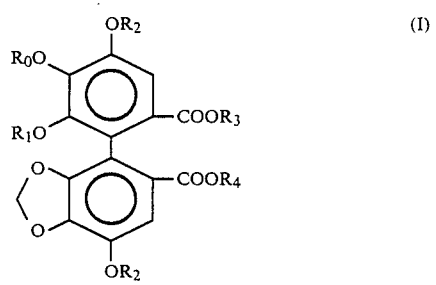

wherein $R_0$ and $R_1$ independently stand for a lower alkyl group, $R_2$ stands for the alkyl group having 1 to 3 carbon atoms, and $R_3$ and $R_4$ independently stand for a hydrogen atom or a lower alkyl group together with a pharmaceutically acceptable carrier.

* * * * *